US00PP29564P3

(12) United States Plant Patent
Smit

(10) Patent No.: US PP29,564 P3
(45) Date of Patent: Jul. 31, 2018

(54) ***APHELANDRA* PLANT NAMED 'WHITE WASH'**

(50) Latin Name: *Aphelandra squarrosa*
Varietal Denomination: White Wash

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 15/530,125

(22) Filed: Dec. 5, 2016

(65) Prior Publication Data

US 2018/0160597 P1 Jun. 7, 2018

(51) Int. Cl.
*A01H 5/00* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

(56) References Cited

PUBLICATIONS

UPOV-PLUTO: Plant Variety Database, Dec. 13, 2017, citation for 'White Wash'. 1 page.*

* cited by examiner

*Primary Examiner* — Susan Beth McCormick Ewoldt
*Assistant Examiner* — Karen M Redden

(57) ABSTRACT

A new cultivar of *Aphelandra* plant named 'White Wash' that is characterized by white/beige leaves with spots of green and undulating leaves with undulating margins and undulations parallel to the secondary veins.

1 Drawing Sheet

Botanical classification: *Aphelandra squarrosa.*
Variety denomination: 'White Wash'.

BACKGROUND OF THE INVENTION

The present invention relates to a new and distinct cultivar of *Aphelandra* plant botanically known as *Aphelandra squarrosa* and hereinafter referred to by the cultivar name 'White Wash'.

'White Wash' originated from the crossing of the female or seed parent, an unnamed proprietary *Aphelandra squarrosa* cultivar and the male or pollen parent, *Aphelandra squarrosa* 'Snow White' (not patented). The crossing was conducted in 2011 in Sappemeer, Netherlands. The resulting seeds were subsequently planted and grown. The cultivar 'White Wash' was selected by the inventor in 2012 in a controlled environment as a single plant within the progeny of the stated cross in a cultivated area of Sappemeer, Netherlands.

Asexual reproduction of the new cultivar 'White Wash' first occurred by leaf cuttings in 2012 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Aphelandra* cultivar 'White Wash'. These traits in combination distinguish 'White Wash' as a new and distinct cultivar apart from other existing varieties of *Aphelandra* known by the inventor.

1. *Aphelandra* 'White Wash' exhibits white/beige leaves with spots of green.
2. *Aphelandra* 'White Wash' exhibits undulating leaves with undulating margins and undulations parallel to secondary veins.

The closest comparison cultivars are *Aphelandra* 'Dania' (not patented) and *Aphelandra* 'Rembrandt' (not patented). 'White Wash' is distinguishable from 'Dania' by the following characteristics:

1. 'White Wash' exhibits white/beige leaves with spots of green. In comparison, the leaves of 'Dania' are green with narrow white veins.
2. 'White Wash' exhibits undulating leaves with undulating margins and undulations parallel to secondary veins. In comparison, the leaves of 'Dania' are mostly smooth with very slight puckering between the veins.

'White Wash' is distinguishable from 'Rembrandt' by the following characteristics:

1. 'White Wash' exhibits white/beige leaves with spots of green. In comparison, the leaves of 'Rembrandt' are green with wide white veins.
2. 'White Wash' exhibits undulating leaves with undulating margins and undulations parallel to secondary veins. In comparison, the leaves of 'Rembrandt' are mostly smooth with very slight puckering between the veins.

'White Wash' is distinguishable from the female parent plant by the following characteristics:

1. 'White Wash' exhibits white/beige leaves with spots of green. In comparison, the leaves of the female parent plant are dark green with white veins.
2. 'White Wash' exhibits undulating leaves with undulating margins and undulations parallel to secondary veins. In comparison, the leaves of the female parent plant are mostly smooth with very slight puckering between the veins.

'White Wash' is distinguishable from the male parent plant by the following characteristics:

1. 'White Wash' exhibits white/beige leaves with spots of green. In comparison, the leaves of the male parent plant are bright white with spots of green.

BRIEF DESCRIPTION OF THE DRAWING

The accompanying photograph illustrates the distinguishing traits of *Aphelandra* 'White Wash'. The photograph shows an overall view of a 20 week old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Aphelandra* cultivar named 'White Wash'. Data was collected in Sappemeer, Netherlands from 20 week old plants grown in a glass greenhouse in 14 cm. diameter containers. The time of year was Summer and the temperature range was 18-25 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'White Wash' has not been tested under all possible conditions and phenotypic differences may be observed with variations in environmental, climatic, and cultural conditions, however, without any variance in genotype.

Botanical classification: *Aphelandra squarrosa* 'White Wash'.

Annual or perennial: Perennial.

Parentage: 'White Wash' resulted from the crossing of the female or seed parent, an unnamed proprietary *Aphelandra squarrosa* cultivar and the male or pollen parent, *Aphelandra squarrosa* 'Snow White'.

Plant type: Pot plant.

Plant shape: Flattened globose.

Growth habit: Upright.

Suitable container size: 10 cm. pots or larger.

Plant height: 16.2 cm.

Plant width: 34.5 cm.

Vigor: Moderate.

Growth rate: Moderate.

Low temperature tolerance: 5° Centigrade.

High temperature tolerance: 35° Centigrade.

Propagation: Leaf cuttings.

Time to initiate roots (summer): 14 days at 21° C.

Time to initiate roots (winter): 21 days at 21° C.

Time to produce a rooted cutting: Leaf cuttings are placed directly into growing container.

Crop time: Approximately 20 weeks in Sappemeer, Netherlands.

Root system: Dense and medium in thickness.

Plant fragrance: None.

Pinching: Not required, but improves branching.

Stem:

*Branching habit.*—Main stem grows from base, no lateral branches.

*Number of main stems per plant.*—Average 1.

*Main stem dimensions.*—9.5 cm. in length and 1.1 cm. in width.

*Internode length.*—1.8 cm.

*Stem shape.*—Rounded.

*Stem texture.*—Smooth.

*Stem luster.*—Glossy.

*Stem pubescence.*—Absent.

*Stem angle.*—Average 0 degrees from vertical.

*Stem strength.*—Strong.

*Stem color* (*young*).—In between 178A and N77B.

*Stem color* (*mature*).—200B to 200C with tinges of N77B.

*Internode color.*—In between 200A and 200B.

Foliage:

*Leaf arrangement.*—Opposite.

*Compound or single.*—Single.

*Quantity of leaves per main stem.*—Average 12.

*Leaf shape.*—Ovate.

*Leaf aspect.*—Undulating with undulating margins and undulations parallel to secondary veins.

*Leaf apex.*—Apiculate.

*Leaf base.*—Attenuate.

*Leaf dimensions.*—17.1 cm. in length and 8.9 cm. in width.

*Texture.*—Glabrous both surfaces.

*Pubescence.*—Absent.

*Leaf luster* (*upper surface*).—Moderately glossy.

*Leaf luster* (*lower surface*).—Matte.

*Leaf rugosity.*—Non-rugose both surfaces.

*Leaf margin.*—Entire, undulating.

*Leaf lobed.*—Not lobed.

*Venation pattern.*—Parallel.

*Young leaf color* (*upper surface*).—174A, veined 157D.

*Young leaf color* (*lower surface*).—178B, veined 155D.

*Mature leaf color* (*upper surface*).—194B, with irregular spots in between 139A and N186A.

*Mature leaf color* (*lower surface*).—189A, lighter toward main vein 198B to 198C.

*Vein color* (*upper surface*).—Main vein 201C to 201D, secondary veins 145C.

*Vein color* (*lower surface*).—Main vein 146B, tinged 183B to 183C towards base, secondary veins 148A.

Petiole:

*Petiole dimensions.*—1.0 cm. in length, 0.6 cm. in width, 0.5 cm. in height.

*Petiole texture.*—Glabrous.

*Petiole luster.*—Slightly glossy.

*Petiole pubescence.*—Absent.

*Petiole strength.*—Moderate.

*Petiole color* (*upper surface*).—N199A, tinged N77B.

*Petiole color* (*lower surface*).—152C to 152D, tinged 183B to 183C.

Flower: 'White Wash' has not produced flowers to date.

Fruit and seed: 'White Wash' has not produced fruit or seed to date.

Disease and pest resistance: Disease and pest resistance has not been observed.

The invention claimed is:

1. A new and distinct variety of *Aphelandra* plant named 'White Wash' as described and illustrated.

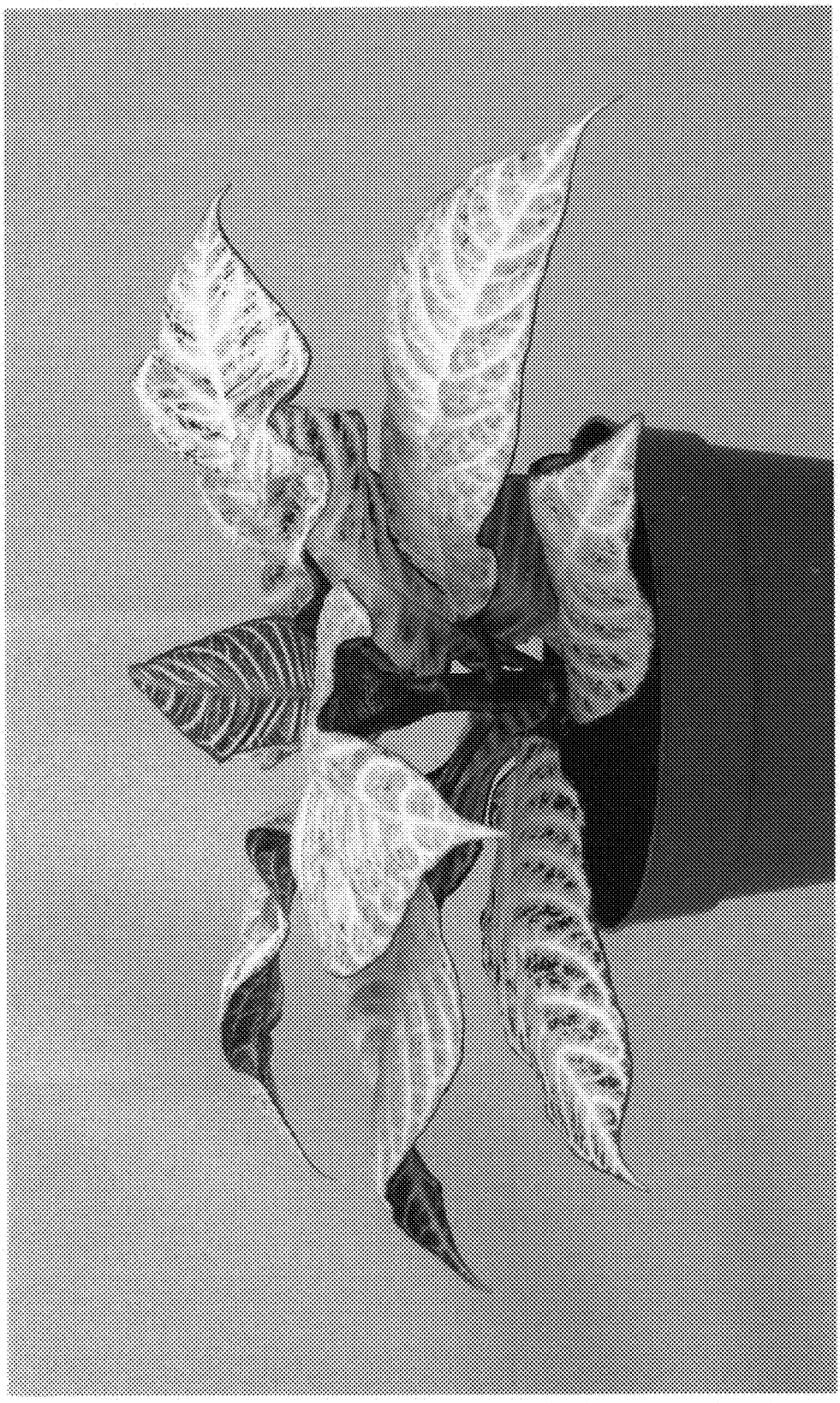

* * * * *